United States Patent [19]
Snead

[11] Patent Number: 5,151,028
[45] Date of Patent: Sep. 29, 1992

[54] TRIPLE PASSAGE ORTHODONTIC BUCCAL TUBE

[75] Inventor: Wilford A. Snead, San Dimas, Calif.

[73] Assignee: Minnesota Mining and Manufacturing Company, St. Paul, Minn.

[21] Appl. No.: 835,880

[22] Filed: Feb. 14, 1992

[51] Int. Cl.$^5$ .............................................. A61C 3/00
[52] U.S. Cl. ................................................ 433/17
[58] Field of Search ........................ 433/8, 10, 16, 17

[56] References Cited

U.S. PATENT DOCUMENTS

| 3,119,182 | 1/1964 | Miller et al. | 32/14 |
|---|---|---|---|
| 3,874,080 | 4/1975 | Wallshein | 32/14 A |
| 4,741,696 | 5/1988 | Cetlin | 433/7 |
| 4,820,151 | 4/1989 | Pospisil | 433/17 |
| 4,927,362 | 5/1990 | Snead | 433/17 |
| 4,963,092 | 10/1990 | Snead | 433/17 |
| 5,057,012 | 10/1991 | Kesling | 433/17 |

Primary Examiner—Gene Mancene
Assistant Examiner—Nicholas D. Lucchesi
Attorney, Agent, or Firm—Gary L. Griswold; Walter N. Kirn; James D. Christoff

[57] ABSTRACT

An orthodontic buccal tube has a first passage for receiving a main arch wire, a second passage for receiving either a lip bumper or a facebow, and a third passage for receiving an auxiliary or segmented arch wire. The second passage includes an enlarged, generally frusto-conical mesial entrance, and the third passage includes a mesial opening that is located at least partially in the enlarged entrance. As such, the third passage can be spaced relatively close to the second passage while the enlarged mesial entrance of the second passage facilitates the insertion of the facebow or the lip bumper.

8 Claims, 3 Drawing Sheets

TRIPLE PASSAGE ORTHODONTIC BUCCAL TUBE

BACKGROUND OF THE INVENTION

1. Field of the Invention

This invention relates to an orthodontic buccal tube having a first passage for receiving a main arch wire, a second passage for a lip bumper or headgear wire and a third passage for an auxiliary arch wire.

2. Description of the Related Art

Orthodontic treatment often involves the use of tiny brackets that are secured to anterior, cuspid and bicuspid teeth. A main arch wire is placed in slots of the brackets to form a track to guide movement of the teeth toward desired positions. Ends of the main arch wire are held in passages formed in small appliances known as buccal tubes that are secured to molar teeth.

Some buccal tubes have passages in addition to the passage for the main arch wire. For example, a passage having a rectangular cross-section may be provided for an auxiliary segmented or utility arch wire that may be used in conjunction with the main arch wire on either the upper or the lower arch. As another option, a round passage may be provided to receive the ends of a facebow or a lip bumper. The facebow is an appliance for the upper arch that is connected to headgear or a neck band to urge the upper arch in a distal, or rearward direction in the mouth. A lip bumper is an appliance fitted between the lower lip and front lower teeth for urging the lower arch in a distal direction.

The space available in the oral cavity next to the molar teeth for receiving buccal tubes is normally limited, and consequently it is desirable to avoid the use of buccal tubes that are relatively bulky. For example, larger buccal tubes when used on the upper arch may rub against the cheek and cause discomfort to the patient. On the lower arch, it is desired to not only avoid impingement with the cheeks but also to avoid contact with any overhanging portion of the cusp of the upper molars when the jaw is closed. In U.S. Pat. No. 4,820,151, assigned to the assignee of the present invention, a hook for anchorage of elastic bands or other auxiliary appliances is gingivally inclined to avoid occlusal interference.

U.S. Pat. No. 4,963,092, also assigned to the assignee of the present invention, describes a buccal tube having a first passage for a main arch wire and a second passage alongside the first passage. The second passage includes a mesial cylindrical portion for receiving ends of a facebow or a lip bumper. The second passage also includes a distal rectangular portion aligned with the cylindrical portion for receiving an auxiliary rectangular arch wire. However, while the buccal tube described in U.S. Pat. No. 4,963,092 has a relatively compact configuration that is advantageous in many instances, an auxiliary arch wire cannot be used simultaneously with use of either a facebow or lip bumper.

A buccal tube described in U.S. Pat. No. 5,057,012 has a first passage for a main arch wire and a second passage for a lip bumper or facebow. The second passage is flared from the distal end to the mesial end, and the mesial end is oval. It is asserted in U.S. Pat. No. 5,057,012 that such construction enhances insertion of a lip bumper or facebow.

However, there exists a need in the art for an orthodontic buccal tube having three passages that can be used simultaneously when desired, and yet is relatively compact in order to fit within the confines of the oral cavity while avoiding contact with opposing teeth, adjacent tissue or otherwise causing discomfort to the patient. Moreover, since lip bumpers or facebows are typically inserted into the tubes by the patient each night before sleeping, it would be desirable to provide a tube that is easy for the patient to use.

SUMMARY OF THE INVENTION

The present invention is directed toward an orthodontic buccal tube that includes a tooth-facing base and a body extending from the base. The body has spaced apart occlusal and gingival side portions. The body includes a first passage between the occlusal and gingival side portions for receiving a main arch wire. The body includes a second passage and a third passage extending alongside the first passage. The second passage includes an enlarged mesial entrance. The third passage includes a mesial opening that is located at least partially within the enlarged entrance.

The enlarged entrance of the second passage facilitates insertion of the ends of a lip bumper or facebow from any one of a number of angles. Further, by locating the mesial opening of the third passage at least partially in the enlarged entrance of the second passage, the second passage and the third passage can be spaced closely together in order to reduce the overall size of the buccal tube. Yet, the buccal tube of the present invention enables the use of both a main arch wire and an auxiliary arch wire simultaneous with use of either a facebow or a lip bumper.

DETAILED DESCRIPTION OF THE PREFERRED EMBODIMENTS

Figure 1:
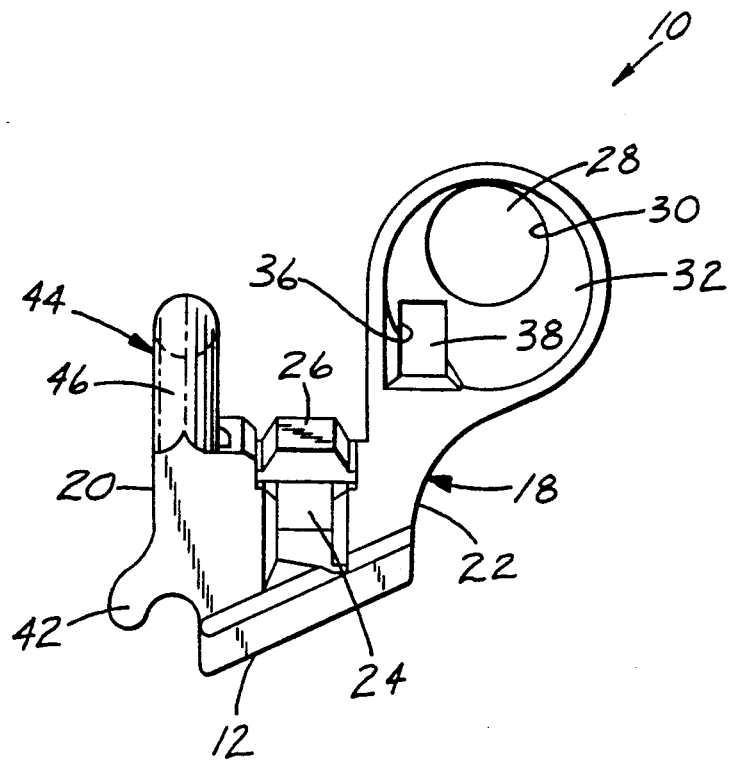
FIG. 1 is a view toward a mesial side of a buccal tube of the present invention taken in a direction along a central axis of a cylindrical lip bumper passage.

A triple passage orthodontic buccal tube 10 in accordance with the invention is illustrated in FIGS. 1-4 and includes a tooth-facing base 12. Typically, and as shown in FIG. 5, the base 12 is welded onto a metallic band 14 that is adapted to encircle a lower first molar tooth 16.

A body 18 extends from the base 12 and includes an occlusal side portion 20 and a gingival side portion 22 that is spaced apart from the occlusal side portion 20. The side portions 20, 22 define therebetween a first elongated passage 24 having a rectangular cross-section as shown in FIGS. 1 and 2 that is adapted to receive a main, rectangular arch wire.

The first passage 24 is initially covered by a cap 26 that may be sheared, when desired, along two frangible side webs in order to open the first passage 24 in a buccal direction. The convertible cap 26, once removed, enables the tube 10 to serve as a bracket when mounted on a first molar tooth. Tubes with convertible caps are often used during treatment of younger children, and the caps are removed once the second molars have erupted and buccal tubes have been mounted on the second molars to function as new anchors for the terminal ends of a longer arch wire. The cap 26 is similar to the convertible cap described in U.S. Pat. No. 4,927,362, assigned to the assignee of the present invention.

The gingival side portion 22 includes a second, elongated passage 28 that has a cylindrical distal section 30 (see, e.g., FIGS. 3 and 4) and an enlarged, somewhat frustoconical mesial entrance 32. The cylindrical section 30 has a diameter adapted to complementally receive a cylindrical terminal end of a lip bumper appliance. A central axis 34 (FIG. 4) of the cylindrical section 30 lies in a plane that is parallel to occlusal and gingival sides of the first passage 24 (in this regard, see also FIGS. 1–3); however, the axis 34 is inclined in such plane relative to a central longitudinal axis of the first passage 24. As shown in FIG. 4, the central longitudinal axis of the first passage 24 is inclined relative to the base 12 such that the distal end of the first passage is offset approximately five degrees in a buccal direction, while the central axis 34 of the cylindrical section 30 is essentially not offset relative to the base 12.

Figure 2:
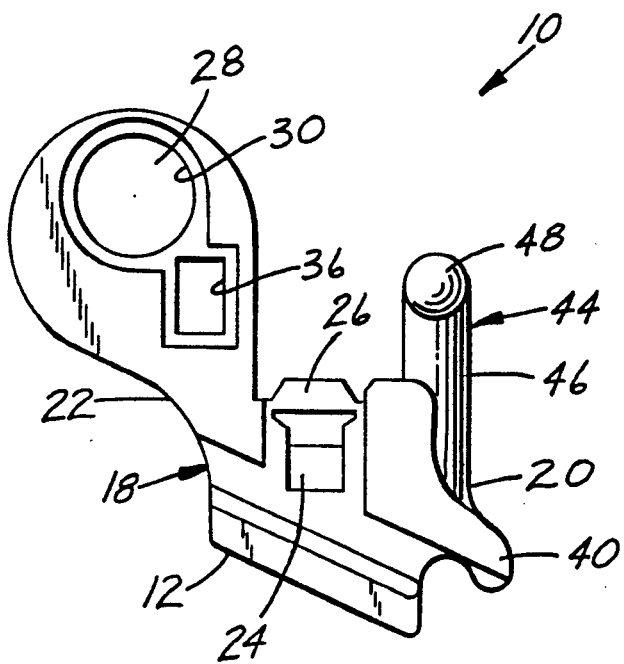
FIG. 2 is a view toward a distal side of the tube shown in FIG. 1 and taken along the central axis of the cylindrical passage.

The enlarged mesial entrance 32 is somewhat frustoconical in configuration, but is asymmetrically oriented relative to the cylindrical section 30 as can be observed by comparing FIGS. 1 and 4. More specifically, and as shown in FIG. 4, a hypothetical reference line 35 extending from the central axis 34 at the mesial end of the cylindrical section 30 and to a point located in the middle of the mesial end of the entrance 32 (where the entrance 32 is also largest in diameter) extends at an angle relative to the axis 34. The enlarged entrance 32 facilitates ease of insertion of the cylindrical end of the lip bumper from any one of a number of angles, and particularly at angles generally parallel to the aforementioned reference line.

The gingival side portion 22 also includes a third passage 36 having a central longitudinal axis parallel to the axis 34 of the cylindrical section 30. The passage 36 has a rectangular cross-sectional configuration adapted to matingly receive the terminal end of an auxiliary or utility arch wire.

Advantageously, the third passage 36 includes a mesial opening 38 that is located partially in the enlarged entrance 32 of the second passage 28 and also partially on the outer, mesial end of the gingival side portion 22. As a consequence, the third passage 36 may be closely spaced to the second passage 28 in order to reduce the overall size of the buccal tube 10. The presence of an auxiliary arch wire in the third passage 36, however, does not unduly hamper the utility of the funnel-shaped mesial entrance 32 that facilitates insertion of the ends of a facebow in the second passage 28.

The mesial end of the third passage 36 is chamfered next to the mesial side of the gingival side portion 22 in areas adjacent the opening 38. Additionally, the distal end of the second passage 28 and the distal end of the third passage 36 are surrounded by stepped or recessed regions as shown in FIGS. 2, 3 and 4.

Figure 3:
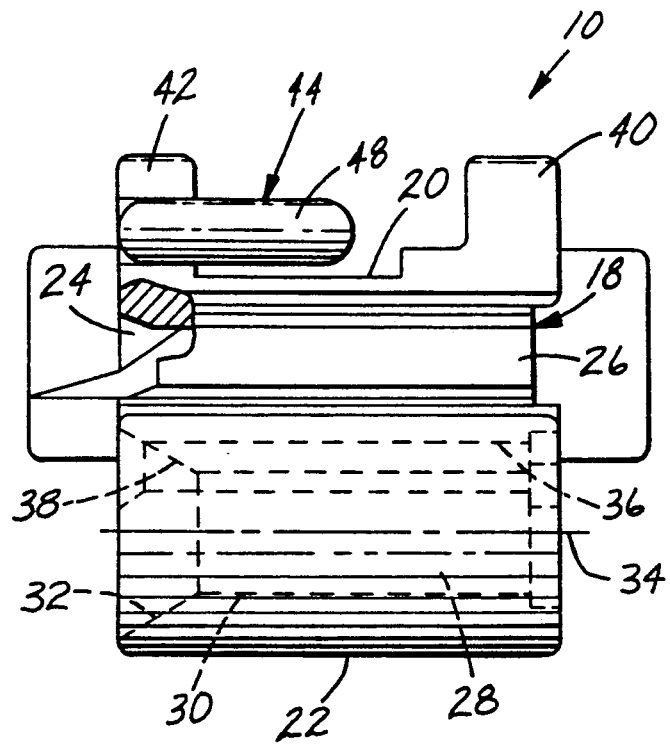
FIG. 3 is a front view taken in a lingual direction of the tube shown in FIGS. 1 and 2.
Figure 4:
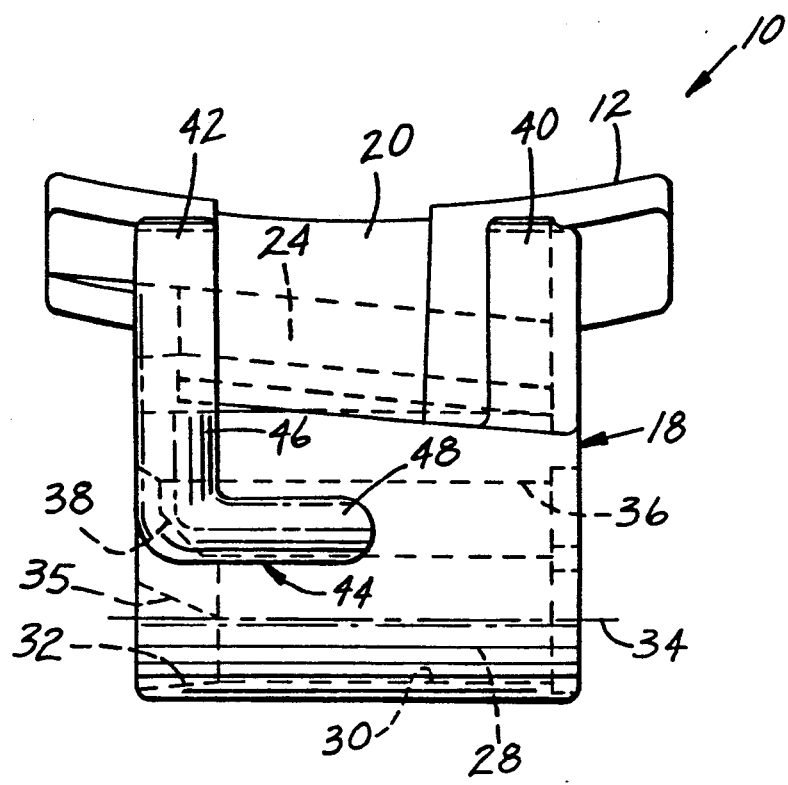
FIG. 4 is a view taken in a generally gingival direction of the tube shown in FIGS. 1-3.
Figure 5:
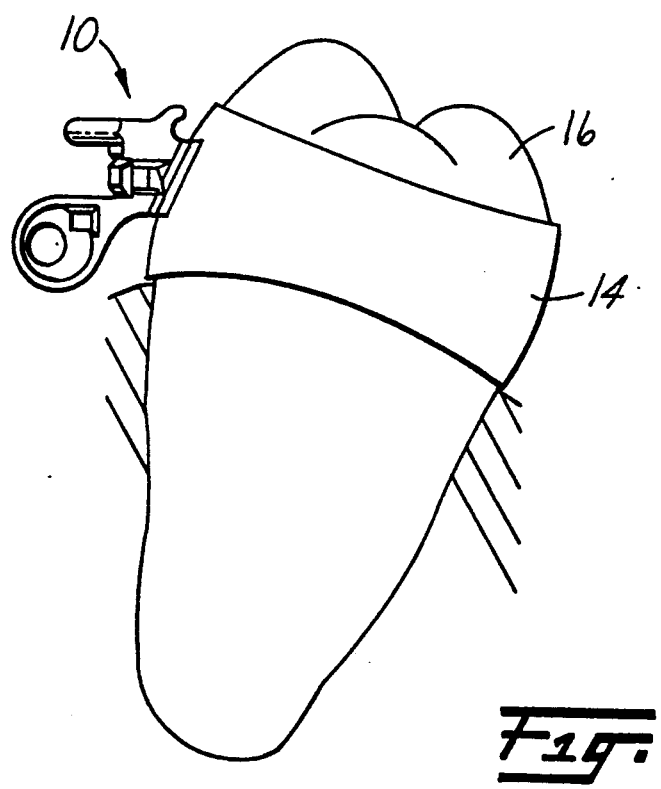
FIG. 5 is a reduced view somewhat similar to FIG. 1, showing the tube mounted on a band that is placed around a molar tooth.

The occlusal side portion 20 has a distal tiewing 40 (FIGS. 2–4) and a mesial tiewing 42 (FIGS. 1 and 3–4). The mesial tiewing 42 is integrally connected to a distally opening hook 44. The hook 44 includes a first leg 46 extending in a generally buccal direction from the mesial tiewing 42, and a second leg 48 extending distally from the first leg 46 in a direction parallel to the axis 34 of the cylindrical section 30. The hook 44 is somewhat similar to the hook described in U.S Pat. No. 4,820,151.

Although not shown, another embodiment of the invention includes a buccal tube adapted for the molar teeth of the upper arch, and is generally similar to the buccal tube 10 for the lower arch. However, the cylindrical section corresponding to the cylindrical section 30 of the tube 10 is sized to receive ends of a facebow appliance.

The buccal tube 10 may be made as a cast or machined structure, but preferably is made using a sintering technique wherein the entire tube 10 is initially formed as a pressed "green" preform of metal powder mixture that has been mixed with a binder to initially hold the powder together. Heating of the preform volatilizes the binder and sinters the metal to yield the final product. The powder mixture is preferably 91.5% by weight of Type 316L stainless steel powder (Anzal NYBY) that is blended with 8.5% by weight of a thermoplastic binder made from waxes, polypropylenes, stearic acid and flow aiding agents. The preform is heated in a series of steps to a temperature of 370° C. to volatilize the binder, and then heated during an additional series of steps to an ultimate temperature of 1260° C. to sinter the powder.

I claim:

1. An orthodontic buccal tube comprising:
   a tooth-facing base;
   a body extending from the base and having spaced apart occlusal and gingival side portions, said body including a first passage between said occlusal and gingival side portions for receiving a main arch wire, said body including a second passage and a third passage, said second passage and said third passage extending alongside said first passage, said second passage including an enlarged mesial entrance, said third passage including a mesial opening that is located at least partially in said enlarged entrance.

2. The orthodontic buccal tube of claim 1 wherein said enlarged mesial entrance has a generally frustoconical configuration.

3. The orthodontic buccal tube of claim 2 wherein said frustoconical configuration is asymmetric relative to a central axis of the second passage.

4. The orthodontic buccal tube of claim 1 wherein said second passage is parallel to said third passage.

5. The orthodontic buccal tube of claim 1 wherein said first passage is inclined relative to said second passage.

6. The orthodontic buccal tube of claim 1 wherein said second passage and said third passage are located on said gingival side portion, and wherein said occlusal side portion includes a distally-opening hook.

7. The orthodontic buccal tube of claim 1 wherein said first passage has a generally rectangular cross-sectional configuration, said second passage includes a cylindrical section, and wherein said third passage has a generally rectangular cross-sectional configuration.

8. The orthodontic buccal tube of claim 1 wherein said third passage is located generally between said first passage and said second passage.

* * * * *